US008772001B2

(12) United States Patent
Olsen et al.

(10) Patent No.: US 8,772,001 B2
(45) Date of Patent: *Jul. 8, 2014

(54) ALCOHOL PRODUCT PROCESSES

(75) Inventors: Hans Sejr Olsen, Holte (DK); Sven Pedersen, Gentofte (DK); Rikke Monica Festersen, Copenhagen K (DK)

(73) Assignee: Novozymes A/S, Bagsvaerd (DK)

( * ) Notice: Subject to any disclaimer, the term of this patent is extended or adjusted under 35 U.S.C. 154(b) by 637 days.

This patent is subject to a terminal disclaimer.

(21) Appl. No.: 12/138,681

(22) Filed: Jun. 13, 2008

(65) Prior Publication Data

US 2009/0017511 A1 Jan. 15, 2009

Related U.S. Application Data

(63) Continuation of application No. 10/797,393, filed on Mar. 10, 2004, now abandoned.

(60) Provisional application No. 60/453,326, filed on Mar. 10, 2003.

(51) Int. Cl.
*C12P 7/06* (2006.01)
*C12P 7/14* (2006.01)
*C12N 9/24* (2006.01)
*C12N 9/26* (2006.01)
*C12N 9/42* (2006.01)

(52) U.S. Cl.
USPC ........... 435/162; 435/161; 435/200; 435/202; 435/209

(58) Field of Classification Search
CPC .............. C12P 7/06; C12P 7/14; C12N 9/24; C12N 9/26; C12N 9/46
USPC .......................... 435/161, 162, 200, 202, 209
See application file for complete search history.

(56) References Cited

U.S. PATENT DOCUMENTS

| | | | |
|---|---|---|---|
| 3,712,820 | A | 1/1973 | Walmsley et al. |
| 3,880,742 | A | 4/1975 | James et al. |
| 3,922,196 | A | 11/1975 | Leach et al. |
| 4,092,434 | A | 5/1978 | Yoshizumi et al. |
| 4,316,956 | A | 2/1982 | Lutzen |
| 4,474,883 | A | 10/1984 | Yamamoto et al. |
| 4,514,496 | A | 4/1985 | Yoshizumi et al. |
| 4,536,477 | A | 8/1985 | Katkocin et al. |
| 4,591,560 | A | 5/1986 | Kainuma et al. |
| 4,618,579 | A | 10/1986 | Dwiggins et al. |
| 4,727,026 | A | 2/1988 | Sawada et al. |
| 5,231,017 | A | 7/1993 | Lantero et al. |
| 5,756,714 | A | 5/1998 | Antrim et al. |
| 2002/0006647 | A1 | 1/2002 | Veit et al. |
| 2002/0073954 | A1 | 6/2002 | Han |
| 2004/0063184 | A1 | 4/2004 | Grichko |
| 2004/0091983 | A1 | 5/2004 | Veit et al. |
| 2004/0234649 | A1 | 11/2004 | Lewis et al. |

FOREIGN PATENT DOCUMENTS

| | | |
|---|---|---|
| EP | 140410 | 5/1985 |
| RU | 2085590 | 5/1995 |
| WO | 02/38787 A2 | 5/2002 |
| WO | WO 03/066816 | 8/2003 |
| WO | WO 03/066826 | 8/2003 |
| WO | WO 03/068976 | 8/2003 |
| WO | WO 2005/092015 | 10/2005 |

OTHER PUBLICATIONS

Abstract of JP 57018991 (1982).
Abstract of JP 7099979 (1995).
Park and Rivera, Biotechnology and Bioengineering, XXIV, pp. 495-500 (1982).
Labout, Starch, vol. 37, pp. 157-161 (1985).
Shiau et al., Applied and Environmental Microbiology, vol. 69, No. 4, pp. 2383-2385 (2003).
Richardson et al., JBC Online, vol. 277, No. 29, pp. 1-16 (2002).
Iefuji et al., Pub Med PMID 6836148, pp. 1-2 (1996).
Haska, ISHS Acta Horiculturae 389; V International Sago Symposium, "Alcohol Production for Sago Starch by Simultaneous Hydrolyzation and Fermentation Using a Raw Starch Digesting Enzyme from *Aspergillus* sp. No. 47 and *Saccharomyces cerevisiae* No. 32" (2004), abstract only.
Pranamuda et al., ISHS Acta Horticultureae 389; V International Sago Symposium "Ethanol Production from Raw Sago Starch Under Unsterile Condition" (2004), abstract only.
Yasmeen et al., National Institute for Biotechnology and Genetic Engineering, Poster Presentation on "Ethanol Production from Raw Corn Starch by Saccharification with Glucoamylase from *Aspergillus niger*, Mutant M 115 and Fermentation with *Saccharomyces cerevisiae*" (2004), abstract only.
Hayashida et al., Applied and Environmental Microbiology, vol. 54, No. 6, pp. 1516-1522 (1988).
Abe et al., Carbohydrate Research, vol. 175, pp. 85-92 (1988).
Suresh et al., Bioprocess Engineering, vol. 21, No. 1, pp. 165-168 (1999).
Oh et al., Korean Journal of Applied Microbiology and Bioengineering, vol. 15, No. 6, pp. 408-413 (1987).
Pyong-Su O et al., Korean Journal of Applied Microbiology and Bioengineering, vol. 14, No. 5, pp. 415-420 (1986).
Haska et al., Starch, vol. 45, No. 7, pp. 241-244 (1993).
Ueda et al., Starch, vol. 27, No. 4, pp. 123-128 (1975).
Shibuya et al., Bioscience Biotechnology Biochemistry, vol. 56, No. 2, pp. 884-889 (1992).
Gray et al., Journal of Bacteriology, vol. 166, No. 2, pp. 635-643 (1986).
Jorgensen et al., Biotechnology Letters, vol. 19, No. 10, pp. 1027-1031 (1997).
Hayashida et al., Agric. Biol. Vo. 46, No. 7, pp. 1947-1950 (1982).
Hayashida et al., Agric. Biol. Ghem. vol. 46, No. 6, pp. 1639-1645 (1982).

(Continued)

*Primary Examiner* — Julie Ha
(74) *Attorney, Agent, or Firm* — Michael W. Krenicky

(57) ABSTRACT

Processes for production of an alcohol product from granular starch comprising a pre-treatment at an elevated temperature below the initial gelatinization temperature of the granular starch followed by simultaneous saccharification and fermentation, and optionally recovery of ethanol, are described.

30 Claims, No Drawings

(56) References Cited

OTHER PUBLICATIONS

Protest under 37 CFR 1.291 with Applicants Consent, filed Feb. 6, 2003.
Arasaratnam et al., Starch, vol. 50, No. 6, pp. 264-266 (1998).
Fujio, Biotechnology and Bioengineering vol. XXVI, pp. 315-319 (1984).
Fujio et al., Biotechnology and Bioengineering, vol. XXVII, pp. 1270-1273 (1985).
Haska et al., Starch, vol. 43, No. 3, pp. 102-107 (1991).
Hayashida et al., Agric. Biol. Chem., vol. 45, No. 12, pp. 2675-2681 (1981).
Hayashida et al., Agric. Biol Chem., vol. 39, No. 11, pp. 2093-2099 (1975).
Hayashida et al., Agric. Biol. Chem., vol. 40, No. 1, pp. 141-146 (1976).
Hayashida et al., Agric. Biol Chem., vol. 42, No. 5, pp. 927-933 (1978).
Ueda et al., Die Starke, No. 11, pp. 374-378 (1974).
Itkor et al., Agric. Biol. Chem., vol. 53, No. 1, pp. 53-60 (1989).
Itkor et al., Biochemical and Biophysical Research Communications, vol. 166, No. 2, pp. 630-636 (1990).
Japanese Patent Laid-Open No. 58/005,145 Date: Jan. 12, 1983 App. 56/100,306 Date: Jun. 27, 1981.
Mikuni et al., Biotechnology and Bioengineering, vol. XXIX, pp. 729-732 (1987).
Norman et al., Cereal: A Renewable Resource, "Ethanol Process Considerations", pp. 651-665.
Robertson et al., Native or Raw Starch Digestion: A Key Step in Energy Efficient Biorefining of Grain.
Saha et al., Biotechnology and Bioengineering, vol. XXV, pp. 1181-1186 (1983).
Ueda et al., Die Starke, No. 4, pp. 123-128 (1975).
Ueda et al., Biotechnology and Bioengineering vol. XXIII, pp. 291-299 (1981).
Ueda et al., Microbiological Sciences, vol. 1, No. 1, pp. 21-24 (1984).
Richardson et al., J. Biol. Chem., vol. 277, Issue 29, pp. 26501-26507 (Jul. 19, 2002).
W.M. Ingledew, Chapter 5, "Alcohol Production by *Saccharomyces cerevisiae*: a yeast primer", pp. 49-87.
Saha et al., J. Ferment. Echnol., vol. 61, No. 1, pp. 67-72 (1983).
Singh et al., J. Basic Microbiol. vol. 35, No. 2, pp. 117-121 (1995).
Lin et al., Biotechnol. Applied Biochem., vol. 28, pp. 61-68 (1998).
Hayashida et al., vol. 10, pp. 529-535 (1974) Abstract only.
Norman et al., "Process considerations for the production of ethanol from cereals" In Cereals: A Renewable Resource (Ed. Pomeranz and Munk) (Published by Am. Ass. Cereal Chemists) (1981).
Haska et al., Mechanism of Hydrolysis of the Treated Sago Starch Granules by Raw Starch Digesting Amylase From *Penicillium brunneum*, Starch, vol. 44, No. 1, pp. 25-28 (1992).
Fang et al., Food Fermentation Industries, vol. 5, pp. 7-12 (1992).
Guo et al, 1994, Chinese Biochemical Journal, 10-3, 259-263—English Abstract attached.

ALCOHOL PRODUCT PROCESSES

CROSS-REFERENCE TO RELATED APPLICATIONS

This application is a continuation of U.S. application Ser. No. 10/797,393 filed Mar. 10, 2004, now abandoned, which claims, under 35 U.S.C. 119, the benefit of U.S. provisional application No. 60/453,326 filed on Mar. 10, 2003, the contents of which are fully incorporated herein by reference.

FIELD OF THE INVENTION

The present invention relates to processes for production of an alcohol product from granular starch comprising a pretreatment at an elevated temperature below the initial gelatinization temperature of the granular starch followed by simultaneous saccharification and fermentation.

BACKGROUND OF THE INVENTION

Granular starch is found in grains, cereals or tubers of plants. The granular starch is in the form of microscopic granules, which are insoluble in water at room temperature. When an aqueous starch slurry is heated, the granules swell and eventually burst, dispersing the starch molecules into the solution. During this "gelatinization" process, there is a dramatic increase in viscosity. Because the solids level is 30-40% in a typical industrial process, the starch has to be thinned or "liquefied" so that it can be handled. This reduction in viscosity is generally accomplished by enzymatic degradation in a process referred to as liquefaction. During liquefaction, the long-chained starch is degraded into smaller branched and linear chains of glucose units (dextrins) by an alpha-amylase.

A conventional enzymatic liquefaction process may be carried out as a three-step hot slurry process. The slurry is heated to between 80-85° C. and thermostable alpha-amylase added to initiate liquefaction. The slurry is then jet-cooked at a temperature between 105-125° C. to complete gelatinization of the slurry, cooled to 60-95° C. and, generally, additional alpha-amylase is added to finalize hydrolysis. The liquefaction process is generally carried out at pH between 5 and 6. Milled and liquefied whole grains are known as mash.

During saccharification, the dextrins from the liquefaction are further hydrolyzed to produce low molecular sugars DP1-3 that can be metabolized by yeast. The hydrolysis is typically accomplished using glucoamylases, alternatively or in addition to glucoamylases, alpha-glucosidases and/or acid alpha-amylases can be used. A full saccharification step typically last up to 72 hours, however, it is common only to do a pre-saccharification of, e.g., 40-90 minutes at a temperature above 50° C., followed by a complete saccharification during fermentation in a process known as simultaneous saccharification and fermentation (SSF).

Fermentation, may be performed using a yeast, e.g., from *Saccharomyces* spp., which added to the mash. When the alcohol product is recovered ethanol, e.g., fuel, potable, or industrial ethanol, the fermentation is carried out, for typically 35-60 hours at a temperature of typically around 32° C. When the alcohol product is beer, the fermentation is carried out, for typically up to 8 days at a temperature of typically around 14° C.

Following fermentation, the mash may be used, e.g., as a beer, or distilled to recover ethanol. The ethanol may be used as, e.g., fuel ethanol, drinking ethanol, and/or industrial ethanol.

It will be apparent from the above discussion that the starch hydrolysis in a conventional alcohol product process is very energy consuming due to the different temperature requirements during the various steps, U.S. Pat. No. 4,316,956 provides a fermentation process for conversion of granular starch into ethanol. European Patent No. 0140410 provides an enzyme composition for starch hydrolysis. The object of the present invention is to provide improved processes for conversion of granular starch into alcohol products.

SUMMARY OF THE INVENTION

The present invention provides methods for producing an alcohol product from granular starch without prior gelatinization of said starch. Accordingly in a first aspect, the invention provides a process for production of an alcohol product comprising the sequential steps of: (a) providing a slurry comprising water and granular starch, (b) holding said slurry in the presence of an acid alpha-amylase and a glucoamylase at a temperature of 0° C. to 20° C. below the initial gelatinization temperature of said granular starch for a period of 5 minutes to 12 hours, (c) holding said slurry in the presence of an acid alpha-amylase, and a glucoamylase, and a yeast at a temperature of between 10° C. and 35° C. for a period of 20 to 250 hours to produce ethanol and (d) optionally recovering the ethanol.

Although not limited to any one theory of operation, the present invention, in particular, process step (b), is believed to result in swelling of starch granules enclosed in the plant cells resulting in the disruption of cell walls and release of the starch granules thereby rendering the starch granules more accessible to further hydration and the action of the enzymes. As hydration progresses through step (b), the acid alpha-amylase degrades the starch granules to produce dextrins, which are degraded by the glucoamylase into glucose. This process continues during step (c) in which the glucose is continuously fermented to ethanol by the yeast, thereby maintaining the concentration of fermentable sugar at a relatively low concentration throughout the fermentation. Without being limited to any one theory of operation, it is believed that due to the low concentration of sugars present during fermentation, the production of glycerol by the yeast is decreased as there is a limited need for glycerol for osmoregulation. In this regard, the present invention may be used to produce an alcohol product which has a reduced glycerol and/or methanol content compared to conventional processes.

The present invention provides a less energy consuming alternative to conventional processes which must employ significant amounts of energy to gelatinize the starch slurry. Other advantages of the present invention include, without limitation, the ability to employ a low pH throughout the process, thus reducing the risk of unwanted microbial growth, and reducing or eliminating the need for expensive equipment to gelatinize the starch, such as, jetting installations and steam plant equipment.

In a second aspect the present invention relates to an enzyme composition comprising an acid alpha-amylase and a glucoamylase, wherein the ratio between the acid alpha-amylase activity and glucoamylase activity is from 0.30 to 5.00 AFAU/AGU wherein an additional enzyme activity is present said enzyme activity is selected from the list consisting of cellulase, xylanase and phytase.

In a third aspect the present invention relates to a use of the enzyme composition of the second aspect in an alcohol product process or a starch hydrolysis process.

In a fourth aspect the present invention relates to a use of an enzyme composition comprising an acid alpha-amylase and a glucoamylase, wherein the ratio between the acid alpha-amylase activity and glucoamylase activity is from 0.30 to 5.00 AFAU/AGU, in an alcohol product process comprising hydrolysis of granular starch.

In a fifth aspect the present invention relates to a mashing process comprising application of an acid alpha-amylase.

DETAILED DESCRIPTION OF THE INVENTION

The term "alcohol product" means a product comprising ethanol, e.g., fuel ethanol, potable and industrial ethanol. However, the alcohol product may also be a beer, which beer may be any type of beer. Preferred beer types comprise ales, stouts, porters, lagers, bitters, malt liquors, happoushu, high-alcohol beer, low-alcohol beer, low-calorie beer or light beer.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called gelatinization begins.

The term "initial gelatinization temperature" means the lowest temperature at which gelatinization of the starch commences. Starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein. S. and Lii. C., Starch/Stärke, Vol. 44 (12) pp. 461-466 (1992).

The polypeptide "homology" means the degree of identity between two amino acid sequences. The homology may suitably be determined by computer programs known in the art, such as, GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for polypeptide sequence comparison are used: GAP creation penalty of 3.0 and GAP extension penalty of 0.1.

The term "acid alpha-amylase" means an alpha-amylase (E.C. 3.2.1.1) which added in an effective amount has activity at a pH in the range of 3.0 to 7.0, preferably from 3.5 to 6.0, or more preferably from 4.0-5.0. Any suitable acid alpha-amylase may be used in the present invention.

In a preferred embodiment, the acid alpha-amylase is an acid fungal alpha-amylase or an acid bacterial alpha-amylase. Preferably the acid fungal alpha-amylase is obtained from a strain of *Aspergillus*, preferably a strain of *Aspergillus niger* or a strain of a strain of *Aspergillus oryzae*. More preferably the acid alpha-amylase is an acid alpha-amylase having at least 70% homology, such as at least 80% or even at least 90% homology to the acid fungal alpha-amylase having the amino acid sequence set forth in SEQ ID NO: 1 or having at least at least at least 70% homology, such as at least 80% or even at least 90% homology to the acid fungal alpha-amylase having the amino acid in the sequence shown in SWISPROT No: P10529.

Most preferably the acid alpha-amylase is an acid fungal alpha-amylase having the amino acid sequence set forth in SEQ ID NO, 1 or variants thereof having one or more amino acid residues which have been deleted, substituted and/or inserted compared to the amino acid sequence of SEQ ID NO: 1; which variants have alpha-amylase activity.

Preferred acid alpha-amylase for use in the present invention may be derived from a strain of *B. licheniformis, B. amyloliquefaciens,* and *B. stearothermophilus.* Also preferred are acid alpha-amylases having an amino acid sequence which has at least 50% homology, preferably at least 60%, 70%, 80%, 85% or at least 90%, e.g., at least 95%, 97%, 98%, or at least 99% homology to the sequences set forth in SEQ ID NO: 2 or SEQ ID NO: 3. Preferably the acid alpha-amylase used for the process of the invention is one of the acid alpha-amylase variants and hybrids described in WO 96/23874, WO 97/41213, and WO 99/19467, such as the *Bacillus stearothermophilus* alpha-amylase (BSG alpha-amylase) variant having the following mutations delta (181-182)+N193F (also denoted I181*+G182*+N193F) compared to the wild type amino acid sequence set forth in SEQ ID NO: 2. The acid bacterial alpha-amylase may also be a hybrid alpha-amylase comprising the 445 C-terminal amino acid residues of the *Bacillus licheniformis* alpha-amylase set forth in SEQ ID NO: 3 and the 37 N-terminal amino acid residues of the alpha-amylase derived from *Bacillus amyloliquefaciens* set forth in SEQ ID NO: 4, which may further have the substitutions G48A+T491+G107A+H156Y+A181T+N190F+I201F+A209V+Q264S using the numbering in SEQ ID NO: 3. Also preferred are alpha-amylase variants derived from *Bacillus amyloliquefaciens* and having at least 50% homology, such as at least 60%, at least 70%, at least 80%, or even 90% homology to the sequence set forth in SEQ ID NO: 4. Especially preferred are variants having one or more of the mutations H154Y, A181T, N190F, A209V and Q264S and/or deletion of two residues between positions 176 and 179, preferably deletion of E178 and G179.

Preferred commercial compositions comprising alpha-amylase include Mycolase from DSM (Gist Brocades), BAN™, TERMAMYL™ SC, FUNGAMYL™, LIQUOZYME™ X and SAN™ SUPER, SAN™ EXTRA L (Novozymes NS) and CLARASE™ L-40,000, DEX-LO™, SPEZYME™ FRED, SPEZYME™ AA, and SPEZYME™ DELTA AA (Genencor Int.).

A glucoamylase (E.C. 3.2.1.3) to be used in the processes of the invention may be derived from a microorganism or a plant. Preferred are glucoamylases of fungal origin such as *Aspergillus* glucoamylases, in particular *A. niger* G1 or G2 glucoamylase (Boel et al., 1984, EMBO J3 (5), p. 1097-1102). Also preferred are variants thereof, such as disclosed in WO 92/00381 and WO 00/04136, the *A. awamori* glucoamylase (WO 84/02921), *A. oryzae* (Agric. Biol. Chem., 1991, 55 (4), p. 941-949), or variants or fragments thereof. Preferred glucoamylases include the glucoamylases derived from *Aspergillus niger,* such as a glucoamylase having 50%, 55%, 60%, 65%, 70%, 75%, 80%, 85% or even 90% homology to the amino acid sequence set forth in WO 00/04136 and SEQ ID NO: 13. Also preferred are the glucoamylases derived from *Aspergillus oryzae,* such as a glucoamylase having 50%, 55%, 60%, 65%, 70%, 75%, 80%, 85% or even 90% homology to the amino acid sequence set forth in WO 00/04136 SEQ ID NO: 2.

Other preferred glucoamylases include *Talaromyces* glucoamylases, in particular derived from *Talaromyces emersonii* (WO 99/28448), *Talaromyces leycettanus* (U.S. Pat. No. Re 32,153), *Talaromyces duponti, Talaromyces thermophilus* (U.S. Pat. No, 4,587,215), *Clostridium,* in particular *C. thermoamylolyticum* (EP135, 138), and *C. thermohydrosulfuricum* (WO 86/01831).

Commercially available compositions composing glucoamylase include AMG 200L; AMG 300 L, SAN™ SUPER, SAN EXTRA L and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

An additional enzyme that may be used in the processes of the invention includes xylanases, cellutases and phytases.

A xylanase used according to the invention may be derived from any suitable organism, including fungal and bacterial organisms, such as *Aspergillus, Disporotrichum, Penicillium, Neurospora, Fusarium* and *Trichoderma*.

Preferred commercially available preparations comprising xylanase include SHEARZYME®, BIOFEED WHEAT®, CELLUCLAST®, ULTRAFLO®, VISCOZYME® (from Novozymes A/S) and SPEZYME® CP (from Genencor Int.).

The cellulase activity (E.C. 3.2.1.4) may be a cellulase of microbial origin, such as derivable from a strain of a filamentous fungus (e.g., *Aspergillus, Trichoderma, Humicola, Fusarium*).

Commercially available preparations comprising cellulase which may be used include CELLUCLAST®, CELLUZYME®, CEREFLO® and ULTRAFLO® (from Novozymes A/S), LAMINEX™ and SPEZYME® CP (from Genencor Int.) and ROHAMENT® 7069 W (from Röhm GmbH).

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., a 3-phytase (E.G. 3.1.3.8), a 6-phytase (E.C. 3.1.3.26) or a 5-phytase (no E.C. number).

Commercially available phytases preferred according to the invention include BIO-FEED PHYTASE™, PHYTASE NOVO™ CT or L (Novozymes A/S), or NATUPHOS™ NG 5000 (DSM).

Another enzyme used in the process may be a debranching enzyme, such as an isoamylase (E.C. 3.2.1.68) or a pullulanase (E.C. 3.2.1.41). Isoamylase hydrolyzes alpha-1,6-D-glucosidic branch linkages in amylopectin and beta-limit dextrins and can be distinguished from pullulanases by the inability of isoamylase to attack pullulan, and by the limited action on alpha-limit dextrins. Debranching enzyme may be added in effective amounts well known to the person skilled in the art.

In a first preferred embodiment of the first aspect, the invention provides a process for production of ethanol, comprising the steps of, (a) providing a slurry comprising water and granular starch, (b) holding said slurry in the presence of an acid alpha-amylase and a glucoamylase at a temperature of 0° C. to 20° C. below the initial gelatinization temperature of said granular starch for a period of 5 minutes to 12 hours, (c) holding said slurry in the presence of an acid alpha-amylase, and a glucoamylase, and a yeast at a temperature of between 30° C. and 35° C. for a period of 20 to 200 hours to produce ethanol, and (d) recovering the ethanol. The steps (a), (b), (c) and (d) are performed sequentially; however, the process may comprise additional steps not specified in this description which are performed prior to, between or after any of steps (a), (b), (c) and (d).

In the first preferred embodiment of the first aspect the temperature under step (c) is between 28° C. and 36° C., preferably from 29° C. and 35° C., more preferably from 30° C. and 34° C., such as around 32° C. and the slurry is held in contact with the acid alpha-amylase, the glucoamylase and the yeast for a period of time sufficient to allow hydrolysis of the starch and fermentation of the released sugars during step (c), preferably for a period of 25 to 190 hours, preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours, such as 85 to 110 hours.

In a second preferred embodiment of the first aspect, the invention provides a process for production of a beer, comprising the steps of: (a) providing a slurry comprising water and granular starch, (b) holding said slurry in the presence of an acid alpha-amylase and a glucoamylase at a temperature of 0° C. to 20° C. below the initial gelatinization temperature of said granular starch for a period of 5 minutes to 12 hours, (c) holding said slurry in the presence of an acid alpha-amylase, and a glucoamylase, and a yeast at a temperature between 10° C. and 18° C. for a period of 20 to 200 hours to produce ethanol. The steps (a), (b), and (c) are performed sequentially, however, the process may comprise additional steps not specified in this description which are performed prior to, between or after any of steps (a), (b), and (c).

In the second preferred embodiment of the first aspect the temperature under step (c) is between 10° C. and 18° C., preferably from 11° C. and 17° C., more preferably from 12° C. and 16° C., such as between 13° C. and 15° C., e.g. around 14° C. and the slurry is held in contact with the acid alpha-amylase, the glucoamylase and the yeast for a period of time sufficient to allow hydrolysis of the starch and fermentation of the released sugars during step (c), preferably for a period of 100 to 230 hours, preferably from 150 to 210 hours, more preferably from 170 to 200 hours.

The enzyme activities may preferably be dosed in form of the composition of the second aspect of the invention.

The acid alpha-amylase is preferably an acid bacterial alpha-amylase and/or an acid fungal alpha-amylase and/or a variant of an acid alpha-amylase derived from a bacterial and/or a fungal source.

The acid alpha-amylase is added in an effective amount, which is a concentration of acid alpha-amylase sufficient for its intended purpose of converting the granular starch in the starch slurry to dextrins, Preferably the acid alpha-amylase is present in an amount of 10-10000 AFAU/kg of DS, in an amount of 500-2500 AFAU/kg of DS, or more preferably in an amount of 100-1000 AFAU/kg of DS, such as approximately 500 AFAU/kg DS. When measured in AAU units the acid alpha-amylase activity is preferably present in an amount of 5-500000 AAU/kg of DS, in an amount of 500-50000 AAU/kg of DS, or more preferably in an amount of 100-10000 AAU/kg of DS, such as 500-1000 AAU/kg DS.

The glucoamylase is added in an effective amount, which is a concentration of glucoamylase amylase sufficient for its intended purpose of degrading the dextrins resulting from the acid alpha-amylase treatment of the starch slurry. Preferably the glucoamylase activity is present in an amount of 20-200 AGU/kg of DS, preferably 100-1000 AGU/kg of DS, or more preferably in an amount of 200-400 AGU/kg of DS, such as 250 AGU/kg DS, When measured in AGI units the glucoamylase activity is preferably present in an amount of 10-100000 AGI/kg of DS, 50-50000 AGI/kg of DS, preferably 100-10000 AGI/kg of DS, or more preferably in an amount of 200-5000 AGI/kg of DS.

Preferably the activities of acid alpha-amylase and glucoamylase are present in a ratio of between 0.3 and 5.0 AFAU/AGU. More preferably the ratio between acid alpha-amylase activity and glucoamylase activity is at least 0.35, at least 0.40, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 2.5, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI. However, the ratio between acid alpha-amylase activity and glucoamylase activity is preferably less than 6.0, less than 5.5, less than 4.5, less than 4.0, less than 3.5, or even less than 3.0 AUU/AGI.

In a preferred embodiment of the first aspect of the invention the step (b) and/or step (c) is performed in the presence of an additional enzyme activity selected from the list consisting of xylanase, cellulase and phytase. The additional enzyme is preferably added together with the acid alpha-amylase and the glucoamylase. Xylanases may be added in amounts of 1-50000 FXU/kg DS, preferably 5-5000 FXU/kg DS, or more preferably 10-500 FXU/kg DS. Cellulases may be added in the amounts of 0.01-500000 EGU/kg DS, preferably from 0.1-10000 EGU/kg DS, preferably from 1-5000 EGU/kg DS, more preferably from 10-500 EGU/kg DS and most preferably from 100-250 EGU/kg DS. The dosage of the phytase may be in the range 0.5-250000 FYT/kg DS, particularly 1-100000 FYT/kg DS, preferably in the range from 5-25000 FYT/kg DS, preferably 10-10000 FYT/kg, such as 100-1000 FYT/kg DS.

In a preferred embodiment the starch slurry comprises water and 5-60% DS (dry solids) granular starch, preferably 10-50% DS granular starch, more preferably 15-40% DS, especially around 20-25% DS granular starch. The granular starch to be processed in the processes of the invention may in particular be obtained from tubers, roots, stems, cobs, legumes, cereals or whole grain. More specifically the granular starch may be obtained from corns cobs, wheat, barley, rye, milo, sago, cassava, tapioca, sorghum, rice, peas, bean, banana or potatoes. Preferred are both waxy and non-waxy types of corn and barley. The granular starch to be processed may preferably comprising milled whole grain or it may be a more refined starch quality, preferably more than 90%, 95%, 97% or 99.5% pure starch. The raw material comprising the starch is preferably milled in order to open up the structure and allowing for further processing. Dry milling as well as wet milling may be used. When wet milling is applied it may be preceded by a soaking, or steeping step. Both dry and wet milling is well known in the art of alcohol manufacturing and is preferred for the processes of the invention. In the second embodiment of the first aspect of the invention wherein the alcohol product is a beer the granular starch may preferably comprise at least 10%, 20%, 30%, 40%, 50%, 60%, 70%, 80% or even at least 90% granular starch derived from malted cereals, e.g., barley malt.

The pH during step (b) and/or (c) is preferably in the range of 3.0 to 7.0, more preferably from 3.5 to 6.0, or most preferably from 4.0-5.0, such as from 4.3 to 4.6.

The slurry is held in contact with the acid alpha-amylase and glucoamylase at an elevated temperature but below the initial gelatinization temperature for a period of time effective to render the starch granules susceptible for enzymatic degradation (step b), preferably for a period of 5 minutes to 12 hours, preferably from 10 minutes to 6 hours, more preferably from 15 minutes to 3 hours, even more preferably from 20 minutes to 1½ hour, such as from 30 minutes to 1¼ hour, from 40 to 70 minutes, and even from 50 to 60 minutes. The temperature during step (b) should always be adjusted to be below the initial gelatinization temperature of the particular granular starch to be processed, and will typically be between 45° C. and 75° C. According to the invention step (b) is conducted at a temperature from 0° C. to 20° C., preferably to from 0° C. 15° C., more preferably from 0° C. to 10° C. or even more preferably from 0° C. to 5° C. below the initial gelatinization temperature of the particular starch to be processed. The actual temperature may be from 45° C. to 75° C., but is preferably from 55° C. to 65° C. Preferably the temperature at which step (b) is conducted is at least 45° C., 46° C., 47° C., 48° C., 49° C. 50° C. 51° C., 52° C., 53° C., 54° C., 55° C., 56° C., 57° C., 58° C. or preferably at least 55° C., and preferably the temperature is no more than 74° C., 73° C., 72° C., 71° C., 70° C., 69° C., 68° C., 67° C., 66° C., 65° C., 64° C., 63° C. or preferably no more than 62° C.

After being subjected to the process of the first aspect of the invention at least 85%, 86%, 87%, 88%, 89%, 90%, 91%, 92%, 93%, 94%, 95%, 96%, 97%, 98%, or preferably 99% of the dry solids of the granular starch is converted into ethanol.

The ethanol may optionally be recovered. The ethanol recovery may be performed by any conventional manner such as, e.g., distillation and may be used as fuel ethanol and/or potable ethanol and/or industrial ethanol.

In a particularly preferred embodiment the granular starch to be processed is derived from dry or wet milled cereal, such as wheat, barley, rye, and/or corn, the starch slurry has a DS of 20-40 percent, the temperature during step (b) is from 50° C. to 60° C., such as 55° C., the duration of step (b) is from 30 minutes to 75 minutes, such as 60 minutes and step (c) is carried out for 60 to 90 hours. The acid alpha amylase is dosed at 300 to 700 AFAU/kg DS, such as 500 AFAU/kg DS and the glucoamylase is dosed at 100 to 500 AGU/kg DS, such as 250 AGU/kg DS. The ratio of acid alpha amylase to glucoamylase is from 1.0 to 3.0 AFAU/AGU or preferably from 1.5 to 2.5 AFAU/AGU, such as approximately 2.0 AFAU/AGU. In AAU/AGI the ratio of acid alpha amylase to glucoamylase is from 1.3 to 4.0 AAU/AGI or preferably from 2.0 to 2.3 AAU/AGI, such as approximately 2.7 AAU/AGI.

In a second aspect the invention provides an enzyme composition which may be used in any process, including the process of the first aspect of the invention, said enzyme composition having a ratio between acid alpha-amylase activity and glucoamylase activity of at least 0.35, at least 0.40, at least 0.50, at least 0.60, at least 0.70, at least 0.80, at least 0.90, at least 1.00, at least 1.20, at least 1.30, at least 1.40, at least 1.50, at least 1.60, at least 1.70, at least 1.80, or even at least 1.85 AFAU/AGU. Preferably said enzyme composition has a ratio between acid alpha-amylase activity and glucoamylase activity is less than 5.00, less than 4.50, less than 4.00, less than 3.00, less than 2.50, or even less than 2.25 AFAU/AGU. Measured in AAU/AGI the ratio of acid alpha amylase to glucoamylase in said enzyme composition is at least 0.45, at least 0.50, at least 0.60, at least 0.70, at least 0.80, at least 0.90, at least 1.00, at least 1.20, at least 1.30, at least 1.40, at least 1.50, at least 1.60, at least 1.70, at least 1.80, at least 1.90, at least 2.00, at least 2.10, at least 2.20, at least 2.30, at least 2.40 or even at least 2.50 AAU/AGI. Preferably said enzyme composition has a ratio between acid alpha-amylase activity and glucoamylase activity is less than 6.50, less than 5.00, less than 4.50, less than 4.00, or even less than 3.50 AAU/AGI.

In a preferred embodiment the composition of the second aspect of the invention further comprises an additional enzyme activity is present, said enzyme activity is selected from the list consisting of cellulase, xylanase and phytase.

Additional Applications

In a fifth aspect of the invention an acid alpha-amylase, such as an acid alpha-amylase derived from a fungus, preferably of the genus *Aspergillus*, preferably from the species *A. niger*, and most preferably having at least 50%, at least 60%, at least 70%, at least 80% or even at least 90% homology to the sequence shown in SEQ ID No: 1 is used in a brewing process.

Brewing processes are well-known in the art, and generally involve the steps of matting, mashing, and fermentation. In the traditional brewing process the malting serves the purpose of converting insoluble starch to soluble starch, reducing complex proteins, generating color and flavor compounds, generating nutrients for yeast development, and the development of enzymes. The three main steps of the malting process are steeping, germination, and kilning.

Steeping includes mixing the barley kernels with water to raise the moisture level and activate the metabolic processes of the dormant kernel. In the next step, the wet barley is germinated by maintaining it at a suitable temperature and humidity level until adequate modification, i.e., such as degradation of starch and activation of enzymes, has been achieved. The final step is to dry the green malt in the kiln.

Mashing is the process of converting starch from the milled barley malt and solid adjuncts into fermentable and unfermentable sugars to produce wort of the desired composition. Traditional mashing involves mixing milled barley malt and adjuncts with water at a set temperature and volume to continue the biochemical changes initiated during the malting process. The mashing process is conducted over a period of time at various temperatures in order to activate the endogenous enzymes responsible for the degradation of proteins and carbohydrates. By far the most important change brought about in mashing is the conversion of starch molecules into fermentable sugars. The principal enzymes responsible for starch conversion in a traditional mashing process are alpha- and beta-amylases. Alpha-amylase very rapidly reduces insoluble and soluble starch by splitting starch molecules into many shorter chains that can be attacked by beta-amylase. The disaccharide produced is maltose.

To day the double-mash infusion system is the most widely used system for industrial production of beer, especially lager type beer. This system prepares two separate mashes. It utilizes a cereal cooker for boiling adjuncts and a mash tun for well-modified, highly enzymatically active malts. As the traditionally mashing processes utilize the endogenous enzymes of the barley malt the temperature is maintained below 70° C. as inactivation of the enzymes would otherwise occur.

After mashing, when all the starch has been broken down, it is necessary to separate the liquid extract (the wort) from the solids (spent grains). Wort separation is important because the solids contain large amounts of protein, poorly modified starch, fatty material, silicates, and polyphenols (tannins). The objectives of wort separation include the following:
  to produce clear wort,
  to obtain good extract recovery, and
  to operate within the acceptable cycle time.

Wort clarity, extraction recovery, and overall cycle times is greatly affected by the standard of the grist, e.g., the barley malt and the types of adjunct, as well as the applied mashing procedure.

Following the separation of the wort from the spent grains the wort may be fermented with brewers yeast to produce a beer.

Further information on conventional brewing processes may be found in "Technology Brewing and Malting" by Wolfgang Kunze of the Research and Teaching Institute of Brewing, Berlin (VLB), 2nd revised Edition 1999, ISBN 3-921690-39-0.

An acid alpha-amylase, such as an acid alpha-amylase derived from a fungus, preferably of the genus *Aspergillus*, preferably from the species *A. niger*, and most preferably having at least 50%, at least 60%, at least 70%, at least 80% or even at least 90% homology to the sequence shown in SEQ ID NO: 1 be applied in any brewing process as a supplement to the enzymes comprised in the malted and/or unmalted grain or in a higher temperature mashing (HTM) process such as the one disclosed in WO 2004/011591.

In the HTM process the temperature regime applied in the initial mashing phase ensures that the activity of the various endogenous enzymes of the barley malt or of the adjunct is significantly reduced or even eliminated. The high temperature process preferably comprises, forming a mash comprising between 5% and 100% barley malt, adding prior to, during or after forming the mash a mashing enzyme composition, attaining within 15 minutes of forming the mash an initial incubation temperature of at least 70° C., followed by incubation of the mash at a temperature of at least 70° C. for a period of time, and separating the wort from the spent grains, Preferably the period of time of mashing is sufficient to achieve an extract recovery of at least 80%. The term "initial incubation temperature" is understood as the temperature regime during the initial part of the incubation in question.

Thus at temperatures in the interval 70° C. to 78° C. only the barley malt alpha- and beta-amylases will exhibit notable activity, and at temperatures above 78° C. the endogenous enzymes activity will be negligible. In such a mashing process the added mashing enzymes will thus constitute a very essential part of or all enzyme activity. According to one embodiment of the fifth aspect of the invention enzyme activities needed for the mashing process to proceed are exogenously supplied and may be added to the mash ingredients, e.g. the water or the grist before forming the mash, or it may be added during or after forming the mash. The enzymes are preferably supplied all at one time at the start of the process; however, one or more of the enzymes may be supplied at one or more times prior to, at the start, or during the process of the sixth aspect of the invention. In addition to an acid alpha-amylase (E.C. 3.2.1.1) the enzyme activities added may comprise one or more of the following activities; a protease (E.C. 3.4.), cellulase (E.C. 3.2.1.4) and a maltose generating enzyme. The maltose generating enzyme is preferably a beta-amylase (E.C. 3.2.1.2) or even more preferably a maltogenic alpha-amylase (E.C. 3.2.1.133).

In yet a preferred embodiment a further enzyme is added, said enzyme being selected from the group consisting of laccase, lipase, glucoamylase, phospholipase, phytase, phytin esterase, pullulanase, and xylanase.

In accordance with the fifth aspect of the invention a starch containing slurry, the mash, is obtained by mixing a grist comprising at least 5%, or preferably at least 10%, or more preferably at least 15%, even more preferably at least 25%, or most preferably at least 35%, such as at least 50%, at least 75%, at least 90% or even 100% (w/w of the grist) barley malt with water. Preferably at least 5%, preferably at least 10%, more preferably at least 20%, even more preferably at least 50%, at least 75% or even 100% of the barley malt is well modified barley malt. In one embodiment the grist comprises other malted grain than barley malt, so that at least 10%, at least 25%, preferably at least 35%, more preferably at least 50%, even more preferably at least 75%, most preferably at least 90% (w/w) of the grist is other malted grain than barley malt.

Prior to forming the mash the malted and/or unmatted grain is preferably milled and most preferably dry milled. In a preferred embodiment the malted and/or unmalted grain used is a husk free (or hull free) variety or the husks are removed from the malted and/or unmalted grain before forming the mash. Removal of husks is preferably applied where the mashing programs comprising temperatures above 75° C., such as at temperatures above 76° C., 77° C., 78° C., 79° C., 80° C., 81° C., 82° C., 83° C., 84° C., 85° C. or even above 86° C.

The water may preferably, before being added to the grist, be preheated in order for the mash to attain the initial incubation temperature at the moment of mash forming. If the temperature of the formed mash is below the initial incubation temperature additional heat is preferably supplied in order to attain the initial incubation temperature. Preferably the initial incubation temperature is attained within 15 minutes, or more preferably within 10 minutes, such as within 9, 8, 7, 6, 5, 4, 2 minutes or even more preferably within 1 minute after the mash forming, or most preferably the initial incubation temperature is attained at the mash forming.

The initial incubation temperature is preferably at least 70° C., preferably at least 71° C., more preferably at least 72° C., even more preferably at least 73° C., or most preferably at least 74° C., such as at least 75° C., at least 76° C., at least 77° C., at least 78° C., at least 79° C., at least 80° C., at least 81° C., such as at least 82° C. A preferred embodiment of the mashing process of the fifth aspect of the invention includes incubating the mash at the initial incubation temperature of at least 70° C. and maintaining a temperature of at least 70° C., preferably at least 71° C., more preferably at least 72° C., even more preferably at least 73° C., or most preferably at least 74° C., such as at least 75° C., at least 76° C., at least 77° C., at least 78° C., at least 79° C., at least 80° C., at least 81° C., at least 82° C., at least 83° C., at least 84° C., or at least 85° C. i.e. a temperature that never falls below 70° C. for the duration of the incubation period. During the incubation period the temperature is preferably held below 100° C., such as below 99° C., 98° C., 97° C., 96° C., 95° C., 94° C., 93° C., 92° C., 91° C., or even below 90° C.

In the mashing process of the fifth aspect of the invention the temperature may be held constant for the duration of the incubation, or, following a period of an essentially constant temperature (the initial incubation temperature) for the first part of the incubation the temperature may be raised, either as a slow continuously increase, or as one or more stepwise increment(s) during the incubation. Alternatively the temperature may be decreased during the incubation. In one embodiment the initial incubation temperature is at least 70° C. and during the incubation the temperature is increased with at least 1° C., 2° C., 3° C., 4° C., 5° C., 6° C., 7° C., 8° C., 9° C. or preferably with at least 10° C., or more preferably with at least 12° C., such as 15° C. In another embodiment the initial incubation temperature is at least 75° C., or preferably at least 80° C., and the temperature is decreased during the incubation with at least 5° C., or preferably with at least 1° C., 2° C., 3° C., 4° C., 5° C., 6° C., 7° C., 8° C., 9° C. or preferably with at least 10° C., or more preferably with at least 15° C. In a particular embodiment the incubation comprises maintaining the mash at a temperature of at least 75° C., preferably at least 76° C., more preferably at least 77° C., even more preferably at least 78° C., such as at least 79° C., at least 80° C., at least 81° C., 82° C., 83° C., 84° C., 85° C., 86° C., 87° C., 88° C., 89° C. or at least 90° C. for a period of at least 1 minute, preferably for at least 5 minutes, more preferably for at least 15 minutes, even more preferably for at least 20 minutes, such as at least 30 minutes, at least 40 minutes, at least 50 minutes, at least 60 minutes, at least 90 minutes, or at least 120 minutes. In another particular embodiment the incubation comprises maintaining the mash at a temperature of at least 75° C., preferably at least 76° C., more preferably at least 77° C., even more preferably at least 78° C., such as at least 79° C., at least 80° C., such as at least 81° C., 82° C., 83° C., 84° C., 85° C., 86° C., 87° C., 88° C., 89° C. or at least 90° C. for at least 1% of the total incubation time, preferably for at least 5%, more preferably for at least 15%, even more preferably for at least 20%, or at least 30%, at least 40%, at least 50%, at least 60%, at least 70%, at least 80%, at least 90%, such as for 100% of the total incubation time. The duration of the incubation is preferably at least 15 minutes, typically between 30 minutes and 2½ hours, e.g. at least 45 minutes, at least 1 hour, at least 1¼ hour, at least 1½ hour, at least 1¾ hour or at least 2 hours.

In the mashing process of the fifth aspect of the invention the grist may in addition to barley malt preferably comprise adjunct such as unmalted barley, or other malted or unmalted grain, such as wheat, rye, oat, corn, rice, milo, millet and/or sorghum, or raw and/or refined starch and/or sugar containing material derived from plants like wheat, rye, oat, corn, rice, milo, millet, sorghum, potato, sweet potato, cassaya, tapioca, sago, banana, sugar beet and/or sugar cane. For the invention adjuncts may be obtained from tubers, roots, stems, leaves, legumes, cereals and/or whole grain. Preferably the adjunct to be added to the mash of the fifth aspect of the invention has gelatinization temperatures at or below the process temperature. If adjuncts such as rice or corn, or other adjuncts with similar high gelatinization temperature, are to be used in the process of the fifth aspect of the invention, they may preferably be cooked separately to ensure gelatinization before being added to the mash of the fifth aspect of the invention, or the gelatinized adjunct starch may be mashed separately from the mash adding appropriate enzymes to ensure saccharification before being added to the mash. Methods for gelatinization and saccharification of brewing adjuncts are well known in the arts. Adjunct comprising readily fermentable carbohydrates such as sugars or syrups may be added to the barley malt mash before, during or after mashing process of the fifth aspect of the invention but is preferably added after the mashing process. Preferably a part of the adjunct is treated with a protease and/or a beta-glucanase before being added to the mash of the fifth aspect of the invention. During the mashing process, starch extracted from the grist is gradually hydrolyzed into fermentable sugars and smaller dextrins. Preferably the mash is starch negative to iodine testing, before extracting the wort.

Following the mashing step of the fifth aspect of the invention obtaining the wort from the mash typically includes straining the wort from the spent grains, i.e. the insoluble grain and husk material forming part of grist. Hot water may be run through the spent grains to rinse out, or sparge, any remaining extract from the grist.

In the embodiment wherein the husks are removed from malted and/or unmalted grain comprised in the grist the wort separation may comprise a centrifugation step.

The wort produced by the mashing process of the fifth aspect of the invention may be fermented to produce a beer. Fermentation of the wort may include pitching the wort with a yeast slurry comprising fresh yeast, i.e. yeast not previously used for the invention or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms. The methods for fermentation of wort for production of beer are well known to the person skilled in the arts.

Preferred beer types comprise ales, strong ales, stouts, porters, lagers, bitters, export beers, malt liquors, happoushu, high-alcohol beer, low-alcohol beer, low-calorie beer or light beer.

The enzymes to be applied in the fifth aspect of present invention should be selected for their ability to retain sufficient activity at elevated temperatures, such as at the process temperature of the processes, as well as for their ability to retain sufficient activity under the moderately acid pH regime in the mash and should be added in effective amounts. The enzymes may be derived from any source, preferably from a plant or an algae, and more preferably from a microorganism, such as from a bacteria or a fungi.

Suitable proteases include microbial proteases, such as fungal and bacterial proteases. Preferred proteases are acidic proteases, i.e., proteases characterized by the ability to hydrolyze proteins under acidic conditions below pH 7.

Contemplated acid fungal proteases include fungal proteases derived from *Aspergillus, Mucor, Rhizopus, Candida, Coriolus, Endothia, Enthomophtra, Irpex, Penicillium, Sclerotium* and *Torulopsis*. Especially contemplated are proteases derived from *Aspergillus niger* (see, e.g., Koaze et al., (1964), Agr. Biol. Chem. Japan, 28, 216), *Aspergillus saitoi* (see, e.g., Yoshida, 1954, J. Agr. Chem. Soc. Japan, 28, 66), *Aspergillus aculeatus* (Hayashida et al., 1977. Agric. Biol. Chem., 42(5), 927-933, *Aspergillus aculeatus* (WO 95/02044), or *Aspergillus oryzae*, such as the pepA protease; and acidic proteases from *Mucor pusillus* or *Mucor miehei*.

Contemplated are also neutral or alkaline proteases, such as a protease derived from a strain of *Bacillus*. A particular protease contemplated for the invention is derived from *Bacillus amyloliquefaciens* and has the sequence obtainable at Swissprot as Accession No. P06832 (SEQ ID NO: 5). Also contemplated are the proteases having at least 90% homology to amino acid sequence obtainable at Swissprot as Accession No. P06832 (SEQ ID NO: 5) such as at least 92%, at least 95%, at least 96%, at least 97%, at least 98%, or particularly at least 99%.

Further contemplated are the proteases having at least 90% homology to amino acid sequence disclosed as SEQ ID NO: 1 in the Danish patent applications PA 2001 01821 and PA 2002 00005, such as at 92%, at least 95%, at least 96%, at least 97%, at least 98%, or particularly at least 99%.

Also contemplated are papain-like proteases such as proteases within E.C. 3.4.22,* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

Proteases may be added in the amounts of 0.1-1000 AU/kg dm, preferably 1-100 AU/kg dm and most preferably 5-25 AU/kg dm.

The cellulase (E.C. 3.2.1.4) may be of microbial origin, such as derivable from a strain of a filamentous fungus (e.g., *Aspergillus, Trichoderma, Humicola, Fusarium*). Specific examples of cellulases include the endo-glucanase (endoglucanase I) obtainable from *H. insolens* and further defined by the amino acid sequence of FIG. 14 in WO 91/17244 and the 43 kD *H. insolens* endo-glucanase described in WO 91/17243.

A particular cellulase to be used in the processes of the fifth aspect of the invention may be an endo-glucanase, such as an endo-1,4-beta-glucanase. Contemplated are beta-glucanases having at least 90% homology to amino acid sequence disclosed as SEQ.ID.NO:1 in Danish patent application PA2002 00130, such as at least 92%, at least 95%, at least 96%, at least 97%, at least 98%, or particularly at least 99%.

Commercially available cellulase preparations which may be used include CELLUCLAST®, CELLUZYME®, CEREFLO® and ULTRAFLO® (available from Novozymes A/S), LAMINEX™ and SPEZYME® CP (available from Genencor Int.) and ROHAMENT® 7069 W (available from Röhm, Germany).

Beta-glucanases may be added in the amounts of 1.0-10000 BGU/kg dm, preferably from 10-5000 BGU/kg dm, preferably from 50-1000 BGU/kg dm and most preferably from 100-500 BGU/kg dm.

A particular alpha-amylase (EC 3.2.1.1) to be used in the processes of the fifth aspect of the invention may be any fungal alpha-amylase, preferably an acid alpha-amylase. Preferably the acid alpha-amylase is derived from a fungus of the genus *Aspergillus*, preferably from the species *A. niger*, and most preferably having at least 50%, at least 60%, at least 70%, at least 80% or even at least 90% homology to the sequence shown in SEQ ID No:1 is used in a brewing process. Fungal alpha-amylases may be added in an amount of 1-1000 AFAU/kg DM, preferably from 2-500 AFAU/kg DM, preferably 20-100 AFAU/kg DM.

Another acid alpha-amylase enzyme to be used in the processes of the fifth aspect of the invention may be a *Bacillus* alpha-amylase. Well-known *Bacillus* alpha-amylases include alpha-amylase derived from a strain of *B. licheniformis, B. amyloliquefaciens*, and *B. stearothermophilus*. Other *Bacillus* alpha-amylases include alpha-amylase derived from a strain of the *Bacillus* sp. NCIB 12289, NCIB 12512, NCIB 12513 or DSM 9375, all of which are described in detail in WO95/26397, and the alpha-amylase described by Tsukamoto et al., Biochemical and Biophysical Research Communications, 151 (1988), pp. 25-31. In the context of the present invention a contemplated *Bacillus* alpha-amylase is an alpha-amylase as defined in WO99/19467 on page 3, line 18 to page 6, line 27. A preferred alpha-amylase has an amino acid sequence having at least 90% homology to SEQ ID NO: 4 in WO99/19467, such as at least 92%, at least 95%, at least 96%, at least 97%, at least 98%, or particularly at least 99%. Most preferred variants of the maltogenic alpha-amylase comprise the variants disclosed in WO99/43794. Contemplated variants and hybrids are described in WO96/23874, WO97/41213, and WO99/19467. Specifically contemplated is a recombinant *B. stearothermophilus* alpha-amylase variant with the mutations; I181*+G182*+N193F. *Bacillus* alpha-amylases may be added in the amounts of 1.0-1000 NU/kg dm, preferably from 2.0-500 NU/kg dm, preferably 10-200 NU/kg dm.

Maltogenic Alpha-amylase

A particular enzyme to be used in the processes of the fifth aspect of the invention is a maltogenic alpha-amylase (E.C. 3.2.1.133). Maltogenic alpha-amylases (glucan 1,4-alpha-maltohydrolase) are able to hydrolyse amylose and amylopectin to maltose in the alpha-configuration. Furthermore, a maltogenic alpha-amylase is able to hydrolyse maltotriose as well as cyclodextrin. Specifically contemplated maltogenic alpha-amylases may be derived from *Bacillus* sp., preferably from *Bacillus stearothermophilus*, most preferably from *Bacillus stearothermophilus* C599 such as the one described in EP 120.693. This particular maltogenic alpha-amylase has the amino acid sequence shown as amino acids 1-686 of SEQ ID NO: 1 in U.S. Pat. No. 6,162,628. A preferred maltogenic alpha-amylase has an amino acid sequence having at least 90% homology to amino acids 1-686 of SEQ ID NO:1 in U.S. Pat. No. 6,162,628 preferably at least 92%, at least 95%, at least 96%, at least 97%, at least 98%, or particularly at least 99%. Most preferred variants of the maltogenic alpha-amylase comprise the variants disclosed in WO99/43794.

Maltogenic alpha-amylases may be added in amounts of 0.1-1000 MANU/kg dm, preferably from 1-100 MANU/kg dm, preferably 5-25 MANU/kg dm.

Another particular enzyme to be used in the processes of the fifth aspect of the invention may be a beta-amylase (E.C. 3.2.1.2).

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7.0. Specifically contemplated beta-amylase include the beta-amylases SPEZYME® BBA 1500, SPEZYME® DBA and OPTIMALT™ ME, OPTIMALT™, BBA from Genencor Int. as well as the beta-amylases NOVOZYM™ WBA from Novozymes A/S. Beta-amylases may be added in effective amounts well known to the person skilled in the art.

A further particular enzyme to be used in the processes of the fifth aspect of the invention may be a glucoamylase (E.C.3.2.1.3) derived from a microorganism or a plant. Preferred are glucoamylases of fungal or bacterial origin selected from the group consisting of *Aspergillus* glucoamylases, in particular *A. niger* G1 or G2 glucoamylase (Boel et al. (1984), EMBO J. 3 (5), p. 1097-1102), or variants thereof, such as disclosed in WO92/00381 and WO00/04136; the *A. awamori* glucoamylase (WO84/02921), *A. oryzae* (Agric. Biol. Chem. (1991), 55 (4), p. 941-949), or variants or fragments thereof. Glucoamylases may be added in effective amounts well known to the person skilled in the art.

Another enzyme of the process of the fifth aspect of the present invention may be a debranching enzyme, such as an isoamylase (E.C. 3.2.1.68) or a pullulanases (E.C. 3.2.1.41). Isoamylase hydrolyses alpha-1,6-D-glucosidic branch linkages in amylopectin and beta-limit dextrins and can be distinguished from pullulanases by the inability of isoamylase to attack pullulan, and by the limited action on alpha-limit dextrins. Debranching enzyme may be added in effective amounts well known to the person skilled in the art.

Materials and Methods
Alpha-amylase activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored grass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference, Acid Alpha-Amylase Activity When used according to the present invention the activity of any acid alpha-amylase may be measured in AFAU (Acid Fungal Alpha-amylase Units). Alternatively activity of acid alpha-amylase may be measured in AAU (Acid Alpha-amylase Units).

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

| Standard conditions/reaction conditions: | |
|---|---|
| Substrate: | Soluble starch. Concentration approx. 20 g DS/L. |
| Buffer: | Citrate, approx. 0.13 M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as calorimetric indicator. Lintner starch is obtained by dilute hydrochloric acid treatment of native starch so that it retains the ability to color blue with iodine. Further details can be found in EP 0140410, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid alpha-amylase an endo-alpha-amylase (1,4-alpha-D-glucan-glucanohydrolase, E.C. 3.2.1.1) hydrolyzes alpha-14-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

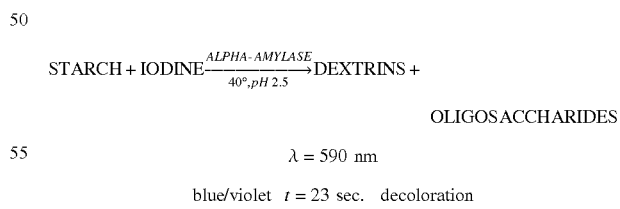

$$STARCH + IODINE \xrightarrow[40°, pH\ 2.5]{ALPHA\text{-}AMYLASE} DEXTRINS +$$

OLIGOSACCHARIDES $\lambda = 590$ nm blue/violet $t = 23$ sec. decoloration

| Standard conditions/reaction conditions: | |
|---|---|
| Substrate: | Soluble starch, approx. 0.17 g/L |
| Buffer: | Citrate, approx. 0.03 M |
| Iodine (I2): | 0.03 g/L |
| $CaCl_2$: | 1.85 mM |
| pH: | 2.50 ± 0.05 |

| Standard conditions/reaction conditions: | |
|---|---|
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S Denmark, which folder is hereby included by reference.

Glucoamylase Activity

Glucoamylase activity may be measured in AGI units or in AmyloGlucosidase Units (AGU).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch-Glucoamylase Method with Subsequent Measurement of Glucose with Glucose Oxidase in "Approved methods of the American Association of Cereal Chemists". Vol. 1-2 AACC, from American Association of Cereal Chemists (2000); ISBN: 1-891127-12-8.

One glucoamylase unit (AGI) is the quantity of enzyme which will form 1 micromol of glucose per minute under the standard conditions of the method.

| Standard conditions/reaction conditions: | |
|---|---|
| Substrate: | Soluble starch, concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |

| AMG incubation: | |
|---|---|
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Xylanolytic Activity

The xylanolytic activity can be expressed in FXU-units determined at pH 6.0 with ramazol-xylan (4-O-methyl-D-glucurono-D-xylan dyed with Remazol Brilliant Blue R Fluka) as substrate.

A xylanase sample is incubated with the remazol-xylan substrate. The background of non-degraded dyed substrate is precipitated by ethanol. The remaining blue color in the supernatant (as determined spectrophotometrically at 585 nm) is proportional to the xylanase activity, and the xylanase units are then determined relatively to an enzyme standard at standard reaction conditions i.e., at 50.0° C., pH 6.0, and 30 minutes reaction time.

A folder EB-SM-352.02/01 describing this analytical method in more detail is available upon request to Novozymes A/S, Denmark, which folder is hereby included by reference.

Cellulolytic Activity

The cellulolytic activity may be measured in endo-glucanase units (EGU), determined at pH 6.0 with carboxymethyl cellulose (CMC) as substrate. A substrate solution is prepared, containing 34.0 g/l CMC (Hercules 7 LFD) in 0.1 M phosphate buffer at pH 6.0. The enzyme sample to be analyzed is dissolved in the same buffer. 5 ml substrate solution and 0.15 ml enzyme solution are mixed and transferred to a vibration viscosimeter (e.g., MIVI 3000 from Sofraser, France), thermostated at 40° C. for 30 minutes. One EGU is defined as the amount of enzyme that reduces the viscosity to one half under these conditions. The amount of enzyme sample should be adjusted to provide 0.01-0.02 EGU/ml in the reaction mixture. The arch standard is defined as 830 EGU/g.

A folder EB-SM-0275.02/01 describing this analytical method in more detail is available upon request to Novozymes A/S, Denmark, which folder is hereby included by reference.

Phytase Activity

The phytase activity is measured in FYT units, one FYT being the amount of enzyme that liberates 1 micromole inorganic ortho-phosphate per min. under the following conditions: pH 5.5, temperature 37° C.; substrate: sodium phylate ($C_6H_6O_{24}P_6Na_{12}$) at a concentration of 0.0050 mole/I.

Proteolytic Activity (AU)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milliequivalent of tyrosine.

A folder AF 4/5 describing the analytical method in more detail is available upon request to Novozymes A/S, Denmark, which folder is hereby included by reference.

Enzyme Preparations

The following enzyme preparations were used:

Bacterial alpha-amylase: An enzyme preparation comprising a polypeptide with alpha-amylase activity (E.C. 3.2.1.1) derived from *B. stearothermophilus* and having the amino acid sequence disclosed as SEQ ID NO: 4 in WO 99/19467. Activity: 120 KNU/g (density=1.20-1.25 g/mL).

A preferred acid fungal alpha-amylase; an enzyme preparations derived from *Aspergillus niger* comprising acid fungal alpha-amylase and some glucoamylase. Activities: 114 AFAU/g, 25 AGU/g (density=1.2 g/mL).

Glucoamylase: an enzyme preparation derived from *Aspergillus niger* comprising glucoamylase and some acid fungal alpha-amylase. Activity: 363 AGU/g, 86 AFAU/g (density=1.2 g/mL).

An enzyme preparation comprising xylanase and cellulase activities derived from *Trichoderma* and *Aspergillus*. Activity: 140 FXU/g+350 EGU/g (density=1.2 g/mL).

EXAMPLE 1

A conventional ethanol process using a traditional pre-liquefaction called the non-pressure cooking (NPC) is compared with the process of the invention. Traditional non-pressure batch cooking processes for production of potable alcohol is described in the Novozymes publication No. 2001-10782-01 entitled "Use of Novozymes enzymes in alcohol production".

A 20% D.S. slurry of the milled barley grain was made in room temperature (RT) tap water.

The NPC pre-treatment of the conventional ethanol process was performed in 6×1-liter tubs with stirring. Bacterial alpha-amylase was added and the tubs were placed in water bath at 65° C. When the temperature in the mash reached 55° C. the heating was increased to heat the mash to 90° C. over 60 minutes. The temperature was then adjusted to 32° C. and 3×250 g mash was portioned in 500 mL blue cap flasks with air locks. To all flasks 0.25 g dry bakers yeast was added (corresponding to 5-10 million vital cells/g mash). Enzyme activities were added according to the table below and each flask was weighed. The flasks were placed in a shaking water bath at 32° C. for 72 hours. At 48 and 72 hours the flasks were weighed and $CO_2$ weight loss measured for monitoring of the fermentation progress. The relationship used between amount of $CO_2$ loss and the weight of ethanol was: $CO_2$ loss (g)×1.045=EtOH (g).

For the process of the invention 500 mL blue cap fermentation flasks each with 250 g slurry was fitted with air locks. Using 6.0 N HCl the pH was adjusted to 4.5 and glucoamylase and acid alpha-amylase was dosed according to table 1. The flasks were held at 55° C. for 60 minutes. The temperature was then adjusted to 32° C. and fermentation was performed and monitored as described above.

TABLE 1

Barley, the weight loss (g) at 48 and 72 hours.
Bacterial alpha-amylase acid (KNU),
acid alpha-amylase (AFAU) and glucoamylase (AGU)
activity was added according to the table.

|  | Traditional non-pressure cooking | Low AFAU/AGU | Process of the invention |
|---|---|---|---|
| KNU/kg DS | 36 | 0 | 0 |
| AFAU/kg DS | 39 | 39 | 540 |
| AGU/kg DS | 163 | 163 | 273 |
| AFAU/AGU | 0.24 | 0.24 | 1.98 |
| Weight loss (g), 48 hours | 9.0 | 11.0 | 14.7 |
| Weight loss (g), 72 hours | 12.2 | 13.0 | 16.4 |
| Ethanol %, 48 hours | 3.76 | 4.60 | 4.60 |
| Ethanol %, 72 hours | 5.10 | 5.43 | 6.86 |

* based on weight loss at 48 and 72 hours, $CO_2$ loss (g) × 1.045 = EtOH (g).

EXAMPLE 2

This example illustrates the use of an enzyme composition of the invention consisting of acid alpha-amylase, glucoamylase, cellulase and xylanase activity.

A 20% D.S. slurry of the milled barley grain was made in RT tap water. For each treatment 2×250 g was portioned in 500 mL blue cap flasks. Using 6 N HCl the pH was adjusted to 4.5. Enzymes activities were added according to table 2 and 3, and a pre-treatment corresponding to step (b) of the invention was carried out for one hour at 55° C. in a shaking water bath. The temperature was adjusted to 32° C. and 0.25 g dry bakers yeast Fermentation was performed and monitored as described above.

TABLE 2

Barley, the weight loss (g) at 48 and 72 hours.
Acid alpha-amylase (AFAU), glucoamylase (AGU),
cellulase (EGU) and xylanase (FXU) activity
was added according to the table.

|  | Low AFAU/AGU | | Process of the invention | |
|---|---|---|---|---|
| AFAU/AGU | 0.24 | 0.24 | 1.98 | 1.98 |
| AFAU/kg DS | 39 | 39 | 540 | 540 |
| AGU/kg DS | 163 | 163 | 273 | 273 |
| FXU/kg DS | 0 | 70 | 0 | 70 |
| EGU/kg DS | 0 | 175 | 0 | 175 |
| Weight loss (g), 48 hours | 9.9 | 11.2 | 12.8 | 14.3 |
| Weight loss (g), 72 hours | 12.1 | 13.8 | 15.5 | 16.5 |
| Ethanol %, 48 hours | 4.14 | 4.68 | 5.35 | 5.98 |
| Ethanol %, 72 hours | 5.06 | 5.77 | 6.48 | 6.90 |

* based on weight loss at 48 and 72 hours, $CO_2$ loss (g) × 1.045 = EtOH (g).

EXAMPLE 3

This example illustrates the process of the invention using various raw materials. A 20% D.S. slurry of the milled grain or corn meal was made in RT tab water. For each treatment 2×250 g was portioned in 500 mL blue cap flasks. Using 6 N HCl the pH was adjusted to 4.5 Enzymes were dosed according to table 3, 4 and 5, and a pre-treatment was carried out for one hour at 55° C. in a shaking water bath. The flasks were cooled to 32° C. and 0.25 g dry bakers yeast added. The flasks were placed in a water bath at 32° C. for 72 hours (90 hours for wheat).

TABLE 3

Rye, the weight loss (g) at 48 hours and at 72 hours. Acid alpha-amylase (AFAU), and glucoamylase (AGU) activity was added according to the table.

| AFAU/kg DS | 39 | 540 |
|---|---|---|
| AGU/kg DS | 163 | 273 |
| AFAU/AGU | 0.24 | 1.98 |
| Weight loss (g), 48 hours | 14.7 | 17.4 |
| Weight loss (g), 72 hours | 16.2 | 19.2 |
| Ethanol %, 48 hours | 6.14 | 7.27 |
| Ethanol %, 72 hours | 6.77 | 8.03 |

* based on weight loss at 48 and 72 hours, $CO_2$ loss (g) × 1.045 = EtOH (g).

TABLE 4

Yellow corn meal, the weight loss (g) at 48 hours and at 72 hours. Acid alpha-amylase (AFAU), and glucoamylase (AGU) activity was added according to the table.

| AFAU/kg DS | 39 | 540 |
|---|---|---|
| AGU/kg DS | 163 | 273 |
| AFAU/AGU | 0.24 | 1.98 |
| Weight loss (g), 48 hours | 12.4 | 14.5 |
| Weight loss (g), 72 hours | 15.6 | 17.5 |
| Ethanol %, 48 hours* | 5.18 | 6.06 |
| Ethanol %, 72 hours* | 6.52 | 7.32 |

*based on weight loss at 48 and 72 hours, $CO_2$ loss (g) × 1.045 = EtOH (g).

TABLE 5

Wheat, the weight losses (g) at 48 hours and at 90 hours. Acid alpha-amylase (AFAU), and glucoamylase (AGU) activity was added according to the table.

| AFAU/kg DS | 39 | 540 |
|---|---|---|
| AGU/kg DS | 163 | 273 |
| AFAU/AGU | 0.24 | 1.98 |
| Weight loss (g), 48 hours | 13.8 | 16.3 |
| Weight loss (g), 90 hours | 16.7 | 18.5 |
| Ethanol %, 48 hours | 5.77 | 6.81 |
| Ethanol %, 72 hours | 6.98 | 7.73 |

* based on weight loss at 48 and 72 hours, $CO_2$ loss (g) × 1.045 = EtOH (g).

EXAMPLE 4

This example illustrates a process of the invention using wheat. A 20% D.S. slurry of milled wheat was made in RT tab water. For each treatment 2×250 g slurry was portioned in 500 mL blue cap flasks. The pH was adjusted to 4.5 using 6 N HCl. Enzyme activities were dosed according to table 6, and the flasks were incubated for one hour at 55° C. in a shaking water bath. The flasks were cooled to 32° C. and 0.25 g dry bakers yeast added. The flasks were placed in a water bath at 32° C. for 72 hours. Weight loss data was recorded. At 50 and 72.5 hours the flasks were weighed and $CO_2$ weight loss measured for monitoring of the fermentation progress. The relationship used between amount of $CO_2$ loss and the weight of ethanol was; $CO_2$ loss (g)×1.045=EtOH (g).

At 100 hours HPLC samples were drawn and the content of ethanol, methanol and glycerol was recorded.

TABLE 6

Wheat; the weight loss (g) at 50 hours and at 72.5 hours. Glucoamylase (AGU), Acid alpha-amylase (AFAU) and bacterial alpha-amylase (KNU) was added according to the table.

| AGU/kg DS | 0.30 | 0.30 | 0.30 | 0.30 | 0.30 | 0.30 | 0.30 |
|---|---|---|---|---|---|---|---|
| AFAU/kg DS | 0.08 | 0.13 | 0.26 | 0.51 | 1.01 | — | — |
| KNU/kg DS | — | — | — | — | — | 0.05 | 0.15 |
| Weight loss (g), 50 hours | 10.67 | 11.01 | 11.71 | 12.53 | 14.14 | 14.68 | 15.55 |
| Weight loss (g), 72.5 hours | 12.53 | 12.90 | 13.78 | 14.80 | 16.90 | 16.62 | 17.52 |
| Ethanol % w/w, 50 hours* | 4.46 | 4.60 | 4.89 | 5.24 | 5.91 | 6.14 | 6.50 |
| Ethanol % w/w, 72.5 hours* | 5.24 | 5.39 | 5.76 | 6.19 | 7.06 | 6.95 | 7.32 |
| Ethanol % w/w, 100 hours** | 6.36 | 6.64 | 7.01 | 7.47 | 7.73 | 8.13 | 8.59 |
| Methanol % w/w, 100 hours** | 0.17 | 0.09 | 0.11 | 0.12 | 0.12 | 0.17 | 0.22 |
| Glycerol % w/w, 100 hours** | 0.52 | 0.54 | 0.49 | 0.54 | 0.53 | 0.65 | 0.72 |
| 3-methyl-1-butanol, 100 hours** | 0.01 | 0.01 | 0.01 | 0.04 | 0.01 | 0.01 | 0.01 |

*based on weight loss at 50 and 72.5 hrs, $CO_2$ loss (g) × 1.045 = EtOH (g)
**based on HPLC at 100 hrs.

EXAMPLE 5

This example demonstrates the use of an acid alpha-amylase in a brewing process. The enzymes used comprised an acid fungal alpha-amylase derived from *Aspergillus niger* having the sequence shown in SEQ ID NO: 1 an alpha-amylase (E.C. 3.2.1.1) from *B. stearothermophilus* having the amino acid sequence disclosed as SEQ ID NO: 4 in WO99/19467 with the mutations: I181*+G182*+N193F, a glucoamylase derived from *Aspergillus niger*, a protease having the amino acid sequence shown as amino acids no. 1-177 of SEQ ID NO. 2 in Danish patent applications WO 2003/048353, a cellulase (E.C. 3.2.1.4), a beta-glucanase having the amino acid sequence shown as SEQ ID NO: 1 in WO 2003/062409.

A xylanase from *Aspergillus aculeatus* having the sequence amino acid disclosed as SEQ ID NO: 2 in WO 94/21785.

The acid alpha-amylase from *Aspergillus niger* SP288 was tested in a mashing set up using both Congress mashing and Higher Temperature Mashing (HTM) conditions. The effect was evaluated on formation of fermentable sugars in the wort, which is a key wort quality parameter. A bacterial heat stable alpha-amylase from *Bacillus stearothermophilus* was applied for comparison. All worts were added a xylanase 5 mg EP/kg DS, betaglucanase 5 mg EP/kg DS and protease 2.5 mg EP/kg DS.

Unless otherwise stated mashing was preformed according to ERG: 4.5.1 using malt grounded according to EBC: 1.1. Mashing trials were performed in 500 ml lidded vessels each containing a mash with 50 g grist and adjusted to a total weight of 450±0.2 g with water preheated to the initial incubation temperature +1° C. During mashing the vessels were incubated in water bath with stirring.

One treatment comprised using Congress mashing described in EBC: 4.5.1. Thus 50.0 g malt is mixed with 200 ml water from beginning, 100 ml water at 70° C. is added when profile reached 70° C. All mashcups are standardized to 450.0 g at the end of mashing, which gives approximately 8.6° P.

The second treatment comprised using HTM as disclosed in WO 2004/011591 with the following temperature profile: an initial incubation temperature of 70° C. for 65 minutes increasing to 90° C., with 1.0° C./min for 20 minutes, followed by 90° C. for 15 minutes and finalized by cooling with 4.5° C./min to 20° C. The recipe applied was: 50.0 g malt added 200 ml water from beginning, at the end of mashing the mash-cups are standardized to 300.0 g, which gives app. 13° P.

Fermentable sugars were analyzed at 8.6° P. using HPLC method equivalent to EBC: 8.7.

TABLE 7

Extract E2, extract in dry malt, % (m/m) from Congress mashing (8.6° P) and HTM (13° P). To all treatments were added xylanase 5 mg EP/kg DS, betaglucanase 5 mg EP/kg DS and Protease 2.5 mg EP/kg DS.
N.B. comparison only intended between enzyme treatments, not between methods.

|  | No additional enzymes | 75 AFAU/kg DS + 61 AGU/kg DS | 75 KNU/kg DS |
|---|---|---|---|
| Congress mashing | 80.90 | 81.79 | 81.97 |
| HTM | 81.42 | 81.23 | 81.33 |

TABLE 8

Overview of fermentable sugar profile from Congress mashing, 8.6° P. To all treatments were added xylanase 5 mg EP/kg DS, beta-glucanase 5 mg EP/kg DS and Protease 2.5 mg EP/kg DS

|  | No additional enzymes | 75 AFAU/kg DS + 61 AGU/kg DS | 75 KNU/kg DS |
|---|---|---|---|
| Glucose | 7.65 | 10.40 | 7.82 |
| Maltose | 43.18 | 43.08 | 43.54 |
| Maltotriose | 8.25 | 7.08 | 9.08 |
| Fructose | 3.24 | 3.29 | 3.40 |
| Sum of fermentable sugars | 62.32 | 63.83 | 63.83 |

TABLE 9

Fermentable sugar profile from HTM mashing, 13° P. To all treatments were added xylanase 5 mg EP/kg DS, beta-glucanase 5 mg EP/kg DS and Protease 2.5 mg EP/kg DS.

|  | No additional enzymes | 75 AFAU/kg DS + 61 AGU/kg DS | 75 KNU/kg DS |
|---|---|---|---|
| Glucose | 10.19 | 14.12 | 10.43 |
| Maltose | 65.98 | 67.10 | 66.46 |
| Maltotriose | 12.61 | 11.07 | 12.89 |
| Fructose | 5.27 | 5.15 | 5.13 |
| Sum of fermentable sugars | 94.05 | 97.44 | 94.91 |

Congress trial (a): SP288 combined with AMG showed good effect on formation of fermentable sugars, as the glucose concentration was increased in wort by the addition of acid alpha-amylase both compared to Termamyl SC and with out adding amylase.

Acid alpha-amylase showed very good effect on formation of fermentable sugars, predominantly the glucose concentration was increased in wort by the addition of acid alpha-amylase both compared to Termamyl SC and with out adding amylase. Overall the sum of fermentable sugars is increased from 94.91 g/L to 97.44 g/L from performance of acid alpha-amylase. This means that an increased part of the extract is now fermentable, which will yield higher alcohol amounts.

The invention claimed is:

1. A process for production of an alcohol product comprising the sequential steps of:
   (a) holding a slurry comprising water and granular starch in the presence of an acid alpha-amylase and a glucoamylase at a temperature of 0° C. to 20° C. below the initial gelatinization temperature of the granular starch for a period between 5 minutes and 12 hours, and
   (b) fermenting the slurry in the presence of an acid alpha-amylase, a glucoamylase and a yeast at a temperature between 10° C. and 35° C. to produce the alcohol product,
   wherein step (a) is performed in the presence of a cellulase and a xylanase.

2. The process of claim 1, further comprising recovering the alcohol product.

3. The process of claim 1, wherein the alcohol product is fuel ethanol, potable ethanol and/or industrial ethanol.

4. The process of claim 1, wherein the temperature during step (b) is between 29° C. and 35° C.

5. The process of claim 1, wherein the pH during step (a) is in the range of 3-7.

6. The process of claim 1, wherein the pH during step (b) is in the range of 3-7.

7. The process of claim 1, wherein the starch slurry has 5-60% DS granular starch.

8. The process of claim 1, wherein the granular starch is obtained from tubers, roots, stems, fruits, seeds or whole grain.

9. The process of claim 1, wherein the granular starch is obtained from corn, cobs, wheat, barley, rye, milo, sago, cassava, manioc, tapioca, sorghum, rice or potatoes.

10. The process of claim 1, wherein the granular starch is obtained from cereals.

11. The process of claim 1, wherein the granular starch is obtained from dry milling or wet milling of whole grain.

12. The process of claim 1, wherein the acid alpha-amylase and the glucoamylase are present in step (a) in a ratio of between 0.3 and 5.0 Acid Fungal Alpha-amylase Units/AmyloGlucosidase Units (AFAU/AGU).

13. The process of claim 1, wherein the acid alpha-amylase and the glucoamylase are present in step (b) in a ratio of between 0.3 and 5.0 Acid Fungal Alpha-amylase Units/AmyloGlucosidase Units (AFAU/AGU).

14. The process of claim 1, wherein the acid alpha-amylase is an acid fungal alpha-amylase.

15. The process of claim 14, wherein the acid fungal alpha-amylase is obtained from a strain of *Aspergillus*.

16. The process of claim 1, wherein the acid alpha-amylase is an acid bacterial alpha-amylase.

17. The process of claim 16, wherein the acid bacterial alpha-amylase is derived from a strain of *B. amyloliquefaciens, B. licheniformis*, or *B. stearothermophilus*.

18. The process of claim 1, wherein the glucoamylase is obtained from a strain of *Aspergillus, Clostridium*, or *Talaromyces*.

19. The process of claim 1, wherein the glucoamylase is obtained from a strain of *Aspergillus niger*.

20. The process of claim 1, further comprising performing step (a) in the presence of a phytase.

21. The process of claim 1, further comprising performing step (b) in the presence of phytase.

22. The process of claim 1, further comprising performing steps (a) and (b) in the presence of a phytase.

23. The process of claim 1, wherein step (b) is performed in the presence of a cellulase and a xylanase.

24. The process of claim 1, wherein the period in step (a) is between 5 minutes and 1¼ hours.

25. The process of claim 1, wherein the period in step (a) is between 5 minutes and 1 hour.

26. The process of claim 1, wherein the period in step (a) is between 40 minutes and 1 hour.

27. The process of claim 1, wherein the period in step (a) is between 50 minutes and 1 hour.

28. The process of claim 1, wherein the fermentation in step (b) is for a period between 20 and 250 hours.

29. The process of claim 1, wherein the temperature during step (a) is 45 to 62° C.

30. The process of claim 1, further comprising performing step (b) in the presence of a protease.

* * * * *

SEQUENCE LISTING

```
<160> NUMBER OF SEQ ID NOS: 5

<210> SEQ ID NO 1
<211> LENGTH: 484
<212> TYPE: PRT
<213> ORGANISM: Aspergillus niger

<400> SEQUENCE: 1

Leu Ser Ala Ala Ser Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asn Glu Ile Tyr Cys Gly Gly Ser Trp Gln Gly Ile Ile Asp His
        35                  40                  45

Leu Asp Tyr Ile Glu Gly Met Gly Phe Thr Ala Ile Trp Ile Ser Pro
    50                  55                  60

Ile Thr Glu Gln Leu Pro Gln Asp Thr Ala Asp Gly Glu Ala Tyr His
```

```
             65                  70                  75                  80
Gly Tyr Trp Gln Gln Lys Ile Tyr Asp Val Asn Ser Asn Phe Gly Thr
                     85                  90                  95
Ala Asp Asn Leu Lys Ser Leu Ser Asp Ala Leu His Ala Arg Gly Met
                    100                 105                 110
Tyr Leu Met Val Asp Val Val Pro Asp His Met Gly Tyr Ala Gly Asn
                    115                 120                 125
Gly Asn Asp Val Asp Tyr Ser Val Phe Asp Pro Phe Asp Ser Ser Ser
            130                 135                 140
Tyr Phe His Pro Tyr Cys Leu Ile Thr Asp Trp Asp Asn Leu Thr Met
145                 150                 155                 160
Val Glu Asp Cys Trp Glu Gly Asp Thr Ile Val Ser Leu Pro Asp Leu
                    165                 170                 175
Asp Thr Thr Glu Thr Ala Val Arg Thr Ile Trp Tyr Asp Trp Val Ala
                180                 185                 190
Asp Leu Val Ser Asn Tyr Ser Val Asp Gly Leu Arg Ile Asp Ser Val
                195                 200                 205
Leu Glu Val Gln Pro Asp Phe Phe Pro Gly Tyr Asn Lys Ala Ser Gly
            210                 215                 220
Val Tyr Cys Val Gly Glu Ile Asp Asn Gly Asn Pro Ala Ser Asp Cys
225                 230                 235                 240
Pro Tyr Gln Lys Val Leu Asp Gly Val Leu Asn Tyr Pro Ile Tyr Trp
                    245                 250                 255
Gln Leu Leu Tyr Ala Phe Glu Ser Ser Ser Gly Ser Ile Ser Asn Leu
                260                 265                 270
Tyr Asn Met Ile Lys Ser Val Ala Ser Asp Cys Ser Asp Pro Thr Leu
            275                 280                 285
Leu Gly Asn Phe Ile Glu Asn His Asp Asn Pro Arg Phe Ala Lys Tyr
            290                 295                 300
Thr Ser Asp Tyr Ser Gln Ala Lys Asn Val Leu Ser Tyr Ile Phe Leu
305                 310                 315                 320
Ser Asp Gly Ile Pro Ile Val Tyr Ala Gly Glu Glu Gln His Tyr Ala
                    325                 330                 335
Gly Gly Lys Val Pro Tyr Asn Arg Glu Ala Thr Trp Leu Ser Gly Tyr
                340                 345                 350
Asp Thr Ser Ala Glu Leu Tyr Thr Trp Ile Ala Thr Asn Ala Ile
            355                 360                 365
Arg Lys Leu Ala Ile Ala Ala Asp Ser Ala Tyr Ile Thr Tyr Ala Asn
            370                 375                 380
Asp Ala Phe Tyr Thr Asp Ser Asn Thr Ile Ala Met Ala Lys Gly Thr
385                 390                 395                 400
Ser Gly Ser Gln Val Ile Thr Val Leu Ser Asn Lys Gly Ser Ser Gly
                    405                 410                 415
Ser Ser Tyr Thr Leu Thr Leu Ser Gly Ser Gly Tyr Thr Ser Gly Thr
                420                 425                 430
Lys Leu Ile Glu Ala Tyr Thr Cys Thr Ser Val Thr Val Asp Ser Ser
            435                 440                 445
Gly Asp Ile Pro Val Pro Met Ala Ser Gly Leu Pro Arg Val Leu Leu
            450                 455                 460
Pro Ala Ser Val Val Asp Ser Ser Ser Leu Cys Gly Gly Ser Gly Arg
465                 470                 475                 480
Leu Tyr Val Glu
```

<210> SEQ ID NO 2
<211> LENGTH: 514
<212> TYPE: PRT
<213> ORGANISM: Bacillus stearothermophilus

<400> SEQUENCE: 2

```
Ala Ala Pro Phe Asn Gly Thr Met Met Gln Tyr Phe Glu Trp Tyr Leu
  1               5                  10                  15

Pro Asp Asp Gly Thr Leu Trp Thr Lys Val Ala Asn Glu Ala Asn Asn
             20                  25                  30

Leu Ser Ser Leu Gly Ile Thr Ala Leu Trp Leu Pro Pro Ala Tyr Lys
         35                  40                  45

Gly Thr Ser Arg Ser Asp Val Gly Tyr Gly Val Tyr Asp Leu Tyr Asp
     50                  55                  60

Leu Gly Glu Phe Asn Gln Lys Gly Ala Val Arg Thr Lys Tyr Gly Thr
 65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380
```

```
Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
        420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
        450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Trp Ser Ile Thr Thr
            485                 490                 495

Arg Pro Trp Thr Asp Glu Phe Val Arg Trp Thr Glu Pro Arg Leu Val
            500                 505                 510

Ala Trp

<210> SEQ ID NO 3
<211> LENGTH: 483
<212> TYPE: PRT
<213> ORGANISM: Bacillus licheniformis

<400> SEQUENCE: 3

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240
```

```
Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 4
<211> LENGTH: 480
<212> TYPE: PRT
<213> ORGANISM: Aspergillus amyloliquefaciens

<400> SEQUENCE: 4

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125
```

```
Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
                180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480
```

<210> SEQ ID NO 5
<211> LENGTH: 499
<212> TYPE: PRT
<213> ORGANISM: Aspergillus oryzae

<400> SEQUENCE: 5

```
Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
```

```
                  20                  25                  30
Tyr Phe Leu Leu Thr Asp Arg Phe Ala Arg Thr Asp Gly Ser Thr Thr
             35                  40                  45
Ala Thr Cys Asn Thr Ala Asp Gln Lys Tyr Cys Gly Gly Thr Trp Gln
 50                  55                  60
Gly Ile Ile Asp Lys Leu Asp Tyr Ile Gln Met Gly Phe Thr Ala
 65                  70                  75                  80
Ile Trp Ile Thr Pro Val Thr Ala Gln Leu Pro Gln Thr Thr Ala Tyr
             85                  90                  95
Gly Asp Ala Tyr His Gly Tyr Trp Gln Gln Asp Ile Tyr Ser Leu Asn
            100                 105                 110
Glu Asn Tyr Gly Thr Ala Asp Leu Lys Ala Leu Ser Ser Ala Leu
            115                 120                 125
His Glu Arg Gly Met Tyr Leu Met Val Asp Val Ala Asn His Met
            130                 135                 140
Gly Tyr Asp Gly Ala Gly Ser Ser Val Asp Tyr Ser Val Phe Lys Pro
145                 150                 155                 160
Phe Ser Ser Gln Asp Tyr Phe His Pro Phe Cys Phe Ile Gln Asn Tyr
                165                 170                 175
Glu Asp Gln Thr Gln Val Glu Asp Cys Trp Leu Gly Asp Asn Thr Val
                180                 185                 190
Ser Leu Pro Asp Leu Asp Thr Thr Lys Asp Val Val Lys Asn Glu Trp
                195                 200                 205
Tyr Asp Trp Val Gly Ser Leu Val Ser Asn Tyr Ser Ile Asp Gly Leu
            210                 215                 220
Arg Ile Asp Thr Val Lys His Val Gln Lys Asp Phe Trp Pro Gly Tyr
225                 230                 235                 240
Asn Lys Ala Ala Gly Val Tyr Cys Ile Gly Glu Val Leu Asp Gly Asp
            245                 250                 255
Pro Ala Tyr Thr Cys Pro Tyr Gln Asn Val Met Asp Gly Val Leu Asn
            260                 265                 270
Tyr Pro Ile Tyr Tyr Pro Leu Leu Asn Ala Phe Lys Ser Thr Ser Gly
            275                 280                 285
Ser Met Asp Asp Leu Tyr Asn Met Ile Asn Thr Val Lys Ser Asp Cys
            290                 295                 300
Pro Asp Ser Thr Leu Leu Gly Thr Phe Val Glu Asn His Asp Asn Pro
305                 310                 315                 320
Arg Phe Ala Ser Tyr Thr Asn Asp Ile Ala Leu Ala Lys Asn Val Ala
                325                 330                 335
Ala Phe Ile Ile Leu Asn Asp Gly Ile Pro Ile Ile Tyr Ala Gly Gln
                340                 345                 350
Glu Gln His Tyr Ala Gly Gly Asn Asp Pro Ala Asn Arg Glu Ala Thr
            355                 360                 365
Trp Leu Ser Gly Tyr Pro Thr Asp Ser Glu Leu Tyr Lys Leu Ile Ala
            370                 375                 380
Ser Ala Asn Ala Ile Arg Asn Tyr Ala Ile Ser Lys Asp Thr Gly Phe
385                 390                 395                 400
Val Thr Tyr Lys Asn Trp Pro Ile Tyr Lys Asp Asp Thr Thr Ile Ala
                405                 410                 415
Met Arg Lys Gly Thr Asp Gly Ser Gln Ile Val Thr Ile Leu Ser Asn
            420                 425                 430
Lys Gly Ala Ser Gly Asp Ser Tyr Thr Leu Ser Leu Ser Gly Ala Gly
            435                 440                 445
```

```
Tyr Thr Ala Gly Gln Gln Leu Thr Glu Val Ile Gly Cys Thr Thr Val
        450                 455                 460

Thr Val Gly Ser Asp Gly Asn Val Pro Val Pro Met Ala Gly Gly Leu
465                 470                 475                 480

Pro Arg Val Leu Tyr Pro Thr Glu Lys Leu Ala Gly Ser Lys Ile Cys
                485                 490                 495

Ser Ser Ser
```